United States Patent [19]

Kishimoto et al.

[11] Patent Number: 4,833,134
[45] Date of Patent: May 23, 1989

[54] CEPHEM COMPOUNDS

[75] Inventors: Shoji Kishimoto, Hyogo; Kiminori Tomimatsu; Michiyuki Sendai, both of Osaka, all of Japan

[73] Assignee: Takeda Chemical Industries, Ltd., Japan

[21] Appl. No.: 84,882

[22] Filed: Aug. 13, 1987

[30] Foreign Application Priority Data

Aug. 19, 1986 [JP] Japan ............................ 61-194794
Jun. 15, 1987 [JP] Japan ............................ 62-148377

[51] Int. Cl.⁴ ............... C07D 501/38; A61K 31/545
[52] U.S. Cl. ............................... 514/206; 540/225; 514/203
[58] Field of Search .............. 540/225; 514/206, 203

[56] References Cited

U.S. PATENT DOCUMENTS 4,521,413 6/1985 Terajii et al. ................... 501/38

Primary Examiner—Nicholas S. Rizzo
Attorney, Agent, or Firm—Wegner & Bretschneider

[57] ABSTRACT

Cephem compounds of the formula:

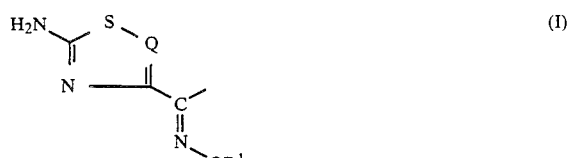
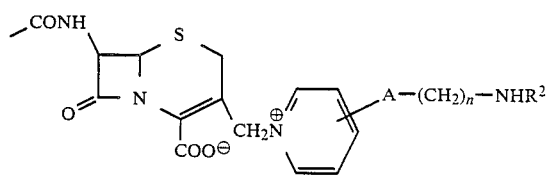

wherein Q stands for a nitrogen atom or CH, $R^1$ stands for a hydrogen atom or an optionally substituted lower alkyl group, $R^2$ stands for a hydrogen atom or a lower alkyl group, A stands for a sulfur atom or NH, and n denotes an integral number ranging from 2 to 4, or salts thereof, and processes for producing them. The compounds (I) or salts thereof show not only excellent antibacterial activities against a wide range of pathogenic bacteria from gram-positive to gram-negative ones, including a variety of strains isolated clinically but also hydrophilic properties, and therefore they are excellent antibiotic substances having desirable water-solubility when used as injections.

8 Claims, No Drawings

CEPHEM COMPOUNDS

This invention relates to novel cephem compounds having excellent antibacterial activities. The cephem compounds of the present invention are used as antibacterial agents.

A variety of cephem compounds having a pyridinium methyl group or pyridinium methyl group having a substituent on its ring at the 3-position and [2-(2-aminothiazol-4-yl) or 2-(5-amino-1,2,4-thiadiazol-3-yl)]-2-hydroxy(or substituted hydroxy)iminoacetamido group at the 7-position simultaneously have so far been synthesized, and patent applications, for instance, U.S. Pat. No. 4520194, No. 4258041, No. 4600772, No. 4431642, No. 4457928, No. 4463000, No. 4367228, No. 4332798, No. 4468515, No. 4567275, No. 4521413 and No. 4278793, EP-47977, EP-88320, EP-111934, Japanese Published unexamined patent application No. 41887/1983, British Pat. No. 2098216, etc., concerning those compounds have been filed. However, no description is found in those applications of the compounds of the present invention having on the pyridine ring in the substituent at the 3-position of the cephem ring an aminoalkylthio or aminoalkylamino group wherein the amino moiety may be substituted with one lower alkyl group.

Cephem-type antibiotics have been widely used for the therapy of diseases of human beings and animals caused by pathogenic bacteria. These compounds are especially useful for the therapy of diseases caused by bacteria resistant to penicillin-type antibiotics as well as for the therapy of penicillin-sensitive patients. In these cases, it is desirable to use cephem-type antibiotics showing activities against both gram-positive and gram-negative bacteria. For this reason, extensive studies on cephem-type antibiotics having a wide antibacterial spectrum have been carried out. At present, several types of the third generation cephalosporin compounds have already been put on the market. However, the antibacterial activities of those compounds are not sufficiently satisfactory, and compounds showing excellent antiacterial activities against both *Staphylococcus aureus* and *Pseudomonas aeruginosa*, compounds showing excellent activities against, for example, meticillin-resistant *Staphylococcus aureus*, compounds showing excellent antibacterial activities against strains producing β-lactamases in a high degree belonging to, for example, *Citrobacter freundii*, *Enterobacter cloacae*, etc. have not yet been found. Therefore, appearance of compounds having excellent and broad antibacterial activities against both gram-positive and gram-negative bacteria including these strains isolated clinically has been desired.

The present invention relates to cephem compounds represented by the general formula;

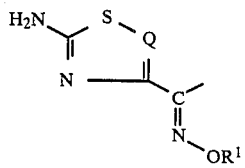

(I)

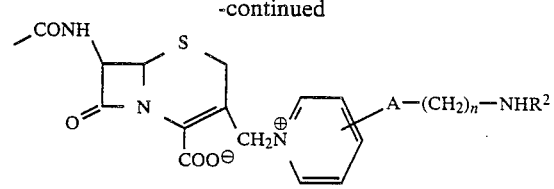

wherein Q stands for a nitrogen atom or CH, $R^1$ stands for a hydrogen atom or an optionally substituted lower alkyl group, $R^2$ stands for a hydrogen atom or a lower alkyl group, A stands for a sulfur atom or NH, and n denotes an integral number ranging from 2 to 4, salts thereof. The compounds (I) or salts thereof have a structural characteristic feature in having at the 3-position of the cephem skeleton a group represented by the formula;

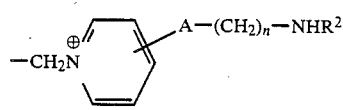

wherein symbols are of the same meaning as defined above. Based on chemical structures brought by specific combinations of the substituents at the 3-position and the acyl group at the 7-position, the compounds of this invention show excellent antibacterial activities against a wide range of pathogenic bacteria from gram-positive to gram-negative ones, including a variety of strains isolated clinically, e.g. clinically isolated strains belonging to *Staphylococcus aureus*, *Pseudomonas aeruginosa*, *Citrobacter freundii*, *Enterobacter cloacae*, etc. The compounds (I) of this invention or salts thereof show hydrophilic properties due to the amino group (or its salts) in the substituent at the 3-position of the above formula. Therefore, they are excellent antibiotic substances having desirable water-solubility when used as injections.

The present invention provides the cephem compounds (I) or salts thereof having thus excellent characteristics.

In the above general formula, Q stands for a nitrogen atom or CH. More specifically, the group represented by the formula

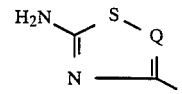

means 5-amino-1,2,4-thiadiazol-3-yl group or 2-aminothiazol-4-yl group.

$R^1$ stands for a hydrogen atom or an optionally substituted lower alkyl group. The lower alkyl group shown by $R^1$ is a straight-chain or branched alkyl group having 1 to 6 carbon atoms, which is exemplified by methyl, ethyl, n-propyl, isopropyl, n-butyl, isobutyl, sec-butyl, tert-butyl, n-pentyl, n-hexyl, etc. The lower alkyl represented by $R^1$ may be substituted by one to three substituents selected from, for example, vinyl group; carboxyl group; $C_{1-6}$-alkoxy-carbonyl group such as methoxycarbonyl, ethoxycarbonyl, etc.; amino group, hydroxyl group; and halogen such as fluorine, chlorine, etc. Examples of the substituted lower alkyl group represented by $R^1$ include allyl, 2-fluoroethyl, 2-chloroethyl, carboxymethyl, 1-methyl-1-carboxyethyl, methoxycarbonylmethyl, 2-aminoethyl, 3-aminopropyl, 4-aminobutyl, 2-hydroxyethyl, 3-hydroxypropyl, 4-hydroxybutyl, etc. $R^1$ is preferably, for example, methyl or ethyl.

$R^2$ stands for a hydrogen atom or a lower alkyl group. As the lower alkyl group shown by $R^2$, use is made of, for example, such groups as those defined for $R^1$, preferably methyl or ethyl. $R^2$ is preferably a hydrogen atom. A stands for a sulfur atom or NH. A is preferably a sulfur atom. The symbol n denotes 2,3 or 4, preferably 3. The group shown by the formula $A\text{-}(CH_2)n\text{-}NHR^2$ wherein all the symbols are of the same meaning as defined above, may be substituted at any of the 2-, 3- or 4-position, preferably at the 4-position, of the pyridinium ring of the pyridinium-1-yl group in the substituent at the 3-position of the cephem nucleus.

The compounds (I) or salts thereof are in the form of syn-isomers ([X]-isomers).

As the salts of the compounds (I), use is preferably made of pharmacologically acceptable ones such as inorganic basic salts, ammonium salts, organic basic salts, inorganic acid addition salts, organic acid addition salts, basic amino acid salts, etc. Examples of inorganic bases capable of forming the inorganic basic salts include alkali metals (e.g. sodium, potassium, etc.), alkaline earth metals (e.g. calcium, etc.), etc.; examples of organic bases capable of forming the organic basic salts include procaine, 2-phenylethylbenzylamine, dibenzylethylenediamine, ethanolamine, diethanolamine, trishydroxymethylaminomethane, polyhydroxyalkylamine, N-methylglucosamine, etc.; examples of inorganic acids capable of forming the inorganic acid addition salts include hydrochloric acid, hydrobromic acid, sulfuric acid, nitric acid, phosphoric acid, etc.; examples of organic acids capable of forming the organic acid addition salts include p-toluenesulfonic acid, methanesulfonic acid, formic acid, trifluoroacetic acid, maleic acid, etc.; and examples of basic amino acids capable of forming the basic amino acid salts include lysine, arginine, ornithine, histidine, etc. Among these salts, basic salts (namely inorganic basic salts, ammonium salts, organic basic salts, basic amino acid salts) mean such basic salts as being formable when an acid group e.g. carboxyl group is present in the substituent $R^1$ of the compounds (I); acid addition salts (namely inorganic acid addition salts, organic acid addition salts) mean such being formable at the amino group in the substituent at the 3-position of the cephem nucleus of the compound (I), or such being formable at the amino group at the 2-position on the thiazol ring or at the 5-position on the thiadiazol ring in the substituent at the 7-position of the cephem nucleus of the compound (I), or such being formable when a basic group e.g. amino group is present in the substituent $R^1$. The acid addition salts include salts in which the 4-position of the cephem nucleus is a carboxyl group (COOH) and the 3-position of the cephem nucleus is a group of the formula

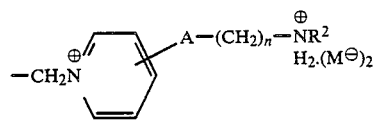

wherein $M^{\ominus}$ stands for anion derived by removing proton ($H^+$) from an inorganic or organic acid, as exemplified by chloride ion, bromide ion, sulfate ion, p-toluenesulfonate ion, methanesulfonate ion, trifluoroacetate ion, etc., formed by allowing an acid to undergo addition to the parts forming an intramolecular salt in the compound (I), namely, the carboxylate site ($COO^{\ominus}$) at the 4-position of the cephem nucleus and the pyridinium portion

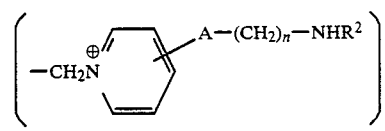

at the 3-position of the cephem nucleous.

Among the compounds (I) of this invention having such characteristic features as mentioned above, those having excellent activities include compounds of the formula:

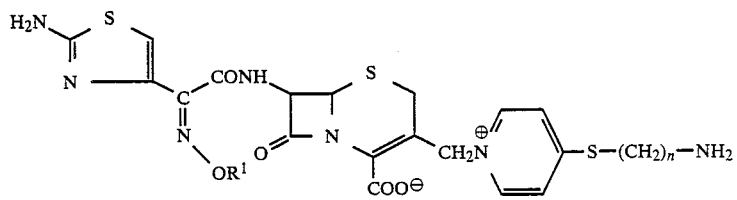

wherein symbols are of the same meanings as defined above, or salts thereof and are, for example, as follows:

(1) 7β-[2-(2-aminothiazol-4-yl)-(Z)-2-ethoxyiminoacetamido]-3-{[4-(3-aminopropylthio)-1-pyridinium]methyl}-3-cephem-4-carboxylate (2) 7β-[2-(2-aminothiazol-4-yl)-(Z)-2-methoxyiminoacetamido]-3-{[4-(3-aminopropylthio)-1-pyridinium]methyl}-3-cephem-4-carboxylate (3) 7β-[2-(5-amino-1,2,4-thiadiazol-3-yl)-(Z)-2-methoxyiminoacetamido]-3-{[4-(3-aminopropylthio)-1-pyridinium]methyl}-3-cephem-4-carboxylate (4) 7β-[2-(2-aminothiazol-4-yl)-(Z)-2-ethoxyiminoacetamido]-3-{[4-(3-aminopropylamino)-1-pyridinium]methyl}-3-cephem-4-carboxylate (5) 7β-[2-(2-aminothiazol-4-yl)-(Z)-2-methoxyiminoacetamido]-3-{[4-(3-methylaminopropylamino)-1-pyridinium]methyl}-3-cephem-4-carboxylate (6) 7β-[2-(5-amino-1,2,4-thiadiazol-3-yl)-(Z)-2-methoxyimino-acetamido]-3-{[4-(3-aminopropylamino)-1-pyridinium]methyl]-3-cephem-4-carboxylate.

Of the compounds set forth above, especially preferable is exemplified by the compound (1).

The compounds (I) or salts thereof are valuable antibiotics showing excellent antibacterial activities against gram-positive and gram-negative bacteria including bacteria isolated clinically, which are used as medicines for humans and domestic animals and can be used safely as antibacterial agents for the therapy and prophylaxis of infections caused by various bacteria.

Further, the compounds (I) or salts thereof can also be added to animal rations as disinfectants for preservation of feeds. They are also usable as antimicrobial preparations for destroying harmful bacteria on medical or dental equipment and are further usable as industrial antiseptics for inhibiting the growth of harmful bacteria in water-based paint, white water in paper mill and so on.

The compounds (I) or salts thereof can be used, singly or in combination with one or more other suitable effective component supplemented with, when necessary, an adjuvant such as a stabilizer, dispersant, etc., as a preparation e.g. capsule, tablet, powder, solution, suspension or elixir. These preparations can be administered non-orally (e.g. intravenously or intramuscularly) or orally.

Injectable preparations can be provided as ampoules or in a unit dosage form using a vessel containing an antibiotic. These preparations may be in a form of suspension, solution or emulsion in an oily or aqueous solvent, and they may contain a conventional auxiliary agent or agents such as a suspending agent, stabilizer and/or dispersant of an appropriate amount. And, the compounds (I) or salts thereof can be used as triturations or powders, by dissolving just before the use in a proper solvent such as sterilized pyrogen-free water.

The compounds (I) or salts thereof can be prepared into tablets, capsules, powders or triturations for oral use, after suitably mixing with a binding agent e.g. syrup, gum arabica, gelatin, sorbitol, tragacanth gum, polyvinyl pyrrolidone, etc., a filler e.g. lactose, sugars, corn-starch, calcium phosphate, sorbitol, glycine, etc., a lubricant e.g. magnesium stearate, talc, polyethylene glycol, silica, etc., a disintegrator e.g. potato starch or a wetting agent e.g. sodium lauryl sulfate, etc. These tablets, powders, etc. can also be subjected to film-coating by per se conventional means. Preparations to be administered orally may be used as liquid preparations such as aqueous or oily suspensions, solutions, emulsions, syrup, elixir, etc.

With these preparations may also be mixed, for example, a conventional anti-oxidant, antiseptic, lubricant, adhesive or flavouring agent. Further, to these preparations may be supplemented any other active component or components (e.g. β-lactam type antibiotics) to show a broader antibiotic spectrum.

To domestic animals, the compounds (I) or salts thereof may be used as preparations to be administered at the site of mammary gland as contained in a substrate for long-lasting effect or prompt release.

The compounds (I) or salts thereof can be used as therapeutic agents of bacterial infections for the therapy and prophylaxis of, for example, respiratory infections, urinary tract infections, suppurative diseases, bile tract infections, intestinal infections, gynecological infections, surgical infections, etc. in human or other mammals. The dosage of the compound (I) or a salt thereof for one day varies with the conditions, body weight of the patient or the route of administration, and, for non-oral administration, it ranges from about 0.5 mg to 80 mg preferably about 1 to 20 mg of the active component [the compound (I) or a salt thereof] per kilogram of body weight of an adult human, which can suitably be administered daily in the form of intravenous injection divided into 2 to 4 times. For oral administration to an adult patient, the suitable daily dosage ranges from about 5 to 100 mg of the active component [the compound (I) or a salt thereof] per kilogram of body weight divided into 1 to 3 times.

The compounds (I) or salts thereof can be produced in accordance with per se known methods (e.g. methods described in EP-135142, U.S. Pat. No. 4258041 and No. 4600772, etc.). They can be produced also by the methods 1 to 4 set forth below.

Method 1

A compound (I) or a salt thereof can be produced by allowing a compound represented by the general formula:

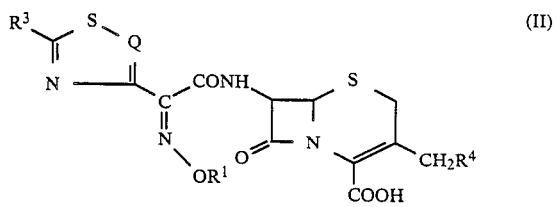

wherein Q and $R^1$ are of the same meaning as defined above: $R^3$ stands for an optionally protected amino group; and $R^4$ stands for a hydroxy group, an acyloxy group, a carbamoyloxy group, a substituted carbamoyloxy group or halogen, or a salt thereof to react with a compound represented by the general formula:

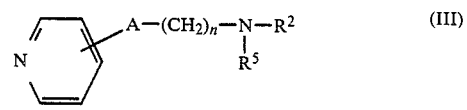

wherein $R^5$ stands for an amino-protective group, and other symbols are of the same meanings as defined above, or a salt thereof, and upon necessity, in an optional order, removing the protective group or groups, converting the resultant salt to a corresponding free acid or free base, and/or converting the resultant free acid or free base to a corresponding pharmacologically acceptable salt.

In the above general formula, the acyloxy group shown by $R^4$ means a group represented by the general formula B-O- wherein B stands for an acyl group derived from an organic carboxylic acid, which is exemplified by formyloxy, acetoxy, propionyloxy, butyryloxy, valeryloxy, pivaloyloxy, chloroacetoxy, dichloroacetoxy, trichloroacetoxy, 3-oxobutyryloxy, 4-chloro-3-oxobutyryloxy, 3-carboxypropionyloxy, 4-carboxybutyryloxy, 3-ethoxycarbamoylpropionyloxy, benzoyloxy, naphthoyloxy, p-methylbenzoyloxy, p-methoxybenzoyloxy, p-chlorobenzoyloxy, o-carboxybenzoyloxy, o-(ethoxycarbonylcarbamoyl) benzoyloxy, o-(ethoxycarbonylsulfamoyl)benzoyloxy, phenylacetyloxy, p-methylphenylacetyloxy, p-methoxyphenylacetyloxy, p-chlorophenylacetyloxy, 2,2-diphenylacetyloxy, thienylcarbonyloxy, furylcarbonyloxy, thiazolylacetyloxy, thienylacetyloxy, furylacetyloxy, etc.; the substituted carbamoyloxy group is exemplified by mono- or di- (an alkyl group having 1 to 6 carbon atoms) substituted carbamoyloxy group, e.g. N-methylcarbamoyloxy, N,N-dimethylcarbamoyloxy, N-ethylcarbamoyloxy, etc., mono-(an aryl group having 6 to 14 carbon atoms) substituted carbamoyloxy group, e.g. N-phenylcarbamoyloxy, etc.;

and the halogen is exemplified by chlorine, bromine, iodine, etc.

A protecting group of the protected amino group shown by $R^3$ and a protecting group of the amino group shown by $R^5$ are exemplified by those usable in the fields of for example β-lactam and peptide, and, among them, preferable ones are, for example, formyl, monochloroacetyl, tert-butoxycarbonyl, benzyloxycarbonyl, p-methoxybenzyloxycarbonyl, p-nitrobenzyloxycarbonyl, 2-trimethylsilylethoxycarbonyl, 2,2,2-trichloroethoxycarbonyl, trityl, o-nitrophenylthio, etc.

In the general formula (II), when an amino group is present in the substituent shown by $R^1$, this amino group is preferably protected. As the protecting group of this amino group, use is made of those as defined in the above $R^3$ and $R^5$. And, when a hydroxyl group is present, this hydroxyl group is preferably protected. As the hydroxyl protecting group, use is suitably made of those employable in the fields of, for example, β-lactam and peptide. Among them, preferable ones are, for example, chloroacetyl, 2,2,2-trichloroethoxycarbonyl, 2-trimethylsilylethoxycarbonyl, benzyl, p-nitrobenzyl, trityl, methylthiomethyl, trimethylsilyl, tert-butyldimethylsilyl, 2-tetrahydropyranyl, 4-methoxy-4-tetrahydropyranyl, etc. Further, when a carboxyl group is present, this carboxyl group is preferably protected, and, as the protecting group of this carboxyl group, use is made of, for example, those employable in the fields of β-lactam and peptide. Among them, preferable ones are, for example, benzyl, p-nitrobenzyl, p-methoxybenzyl, benzhydryl, 2-methylsulfonylethyl, 2-trimethylsilylethyl, 2,2,2-trichloroethyl, trityl, trimethylsilyl, etc.

As salts of the compound (II), use is made of, for example, those with such bases as accelerating the reaction or neutralizing acids formed during the reaction or serving to make the starting materials to be readily soluble. These bases include, for example, tertiary amine e.g. triethylamine, tri-n-butylamine, diisopropylethylamine, etc., alkali metal hydrogencarbonate e.g. sodium hydrogencarbonate, potassium hydrogencarbonate, etc. These bases may be added to the reaction system together with the compound (II) for the purpose mentioned as above, and usually the added amount is preferably within the range of from about 1 to 5 times mols relative to the compound (II). As salts of the compound (III), use is made of, for example, inorganic acid addition salts such as hydrochloride, hydrobromide, sulfate, nitrate, phosphate, etc., and organic acid addition salts such as formate, acetate, trifluoroacetate, methanesulfonate, p-toluenesulfonate, etc.

(1): $R^4$=hydroxyl group

In this reaction, the compound (III) or a salt thereof is employed in an amount of about 1 to 10 mols, preferably about 1 to 5 mols relative to 1 mol of the compound (II) or a salt thereof. This reaction is usually carried out in an organic solvent which does not adversely affect the reaction. As the organic solvents which do not adversely affect the reaction, use is made of, for example, amides such as formamide, dimethylformamide, dimethylacetamide, etc., halogenated hydrocarbons such as dichloromethane, chloroform, 1,2-dichloroethane, etc., ethers such as diethylether, tetrahydrofuran, dioxane, etc., esters such as methyl acetate, ethyl acetate, isobutyl acetate, methyl propionate, etc., nitriles such as acetonitrile, propionitrile, etc., nitro compounds such as nitromethane, nitroethane, etc., ketones such as acetone, methyl ethyl ketone, etc., aromatic hydrocarbons such as benzene, toluene, etc., and they may be used singly or in combination of two or more species in a suitable ratio. Especially preferably ones include, for example, dichloromethane, tetrahydrofuran, acetonitrile, formamide, dimethylformamide, etc., or a mixture solvent of dimethylformamide and acetonitrile, a mixture solvent of dichloromethane and acetonitrile, a mixture solvent of dichloromethane and tetrahydrofuran, etc.

For accelerating this reaction, for example a cyclic phosphorus compound described in U.S. Pat. No. 4642365 or phosphorous ester can be used. More specifically stating, for example, a cyclic phosphorus compound represented by the general formula:

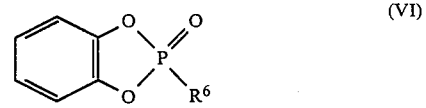

(VI)

wherein $R^6$ stands for phenyl group or a lower alkoxy group, can be used. In the general formula (VI), as the lower alkoxy group shown by $R^6$, use is made of, for example, alkoxy groups of 1 to 4 carbon atoms such as methoxy, ethoxy, propoxy, isobutoxy, etc. Among the cyclic phosphorus compounds (VI), are preferable, for example, methyl o-phenylene phosphate, ethyl o-phenylene phosphate, 2-phenyl-2-oxo-1,3,2-benzodioxaphosphole, etc. The compound (VI) is used in an amount of about 1 mol to 10 mols preferably about 1 mol to 6 mols relative to 1 mol of the compound (II) or a salt thereof. When the compound (VI) is employed, it is preferable to react the compound (II) or a salt thereof, the compound (III) or a salt thereof and the compound (VI) in an organic solvent as mentioned above. More specifically, the compound (II) or a salt thereof and the compound (III) or a salt thereof are mixed in an organic solvent, to which is then added the compound (VI) or its organic solvent solution, or the compound (III) or a salt thereof and the compound (VI) are mixed in a organic solvent, to which is then added the compound (II) or a salt thereof or its organic solvent solution, to thereby carry out this invention.

The reaction temperature varies with the amount, kinds and any other factors of the starting compound (II) or a salt thereof, the compound (III) or a salt thereof, the cyclic phosphorus compound (VI), the organic solvent, the base, etc. then employed, and it usually ranges from about −80° C. to 60° C. The reaction time may be in the range of from 1 minute to about 24 hours.

(2): $R^4$=acyloxy group, carbamoyloxy group, substituted carbamoyloxy group

Preferable solvents are water or a mixed solvent of a water-miscible organic solvent and water. Among water-miscible organic solvents, preferable ones are, for example, acetone, methyl ethyl ketone, acetonitrile, etc.

The compound (III) or a salt thereof is used usually in an amount of about 1 to 5 mols, preferably about 1 to 3 mols relative to 1 mol of the compound (II) or a salt thereof. The reaction is carried out at temperatures ranging from about 10° C. to 100° C., preferably within a range of from about 30° C. to 80° C. The reaction time usually ranges from about 30 minutes to about 5 days, preferably from about 1 hour to 5 hours. The reaction may advantageously be carried out at a pH of 2 to 8, preferably around neutral pH, namely 5 to 8. This reaction proceeds more easily usually in the presence of about 2 to 30 equivalents of an iodide or a thiocyanate. As the iodide, use may be made of sodium iodide, potassium iodide, etc., and as the thiocyanate, use may be made of sodium thiocyanate, potassium thiocyanate, etc. Besides the above-mentioned compounds, a quaternary ammonium salt having a surfactant action, for example, trimethyl benzylammonium bromide, triethyl benzylammonium bromide, triethyl benzylammonium hydroxide, etc. may be added to the reaction system to allow the reaction to proceed smoothly.

(3): $R^4$=halogen

Preferable solvents are afore-mentioned ethers, esters, halogenated hydrocarbons, aromatic hydrocarbons, amides, ketones, nitriles, water, alcohols such as methanol, ethanol, propanol, etc. The compound (III) or a salt thereof is used usually in an amount of about 1 to 5 mols, preferably about 1 to 3 mols relative to 1 mol of the compound (II) or a salt thereof. The reaction is conducted at temperatures ranging from about 0° to 80° C., preferably from about 20° to 60° C. The reaction time usually ranges from about 30 minutes to 15 hours, preferably from about 1 to 5 hours. For accelerating the reaction, the reaction can be conducted in the presence of a dehydrohalogenating agent. As the dehydrohalogenating agent, use is made of, for example, inorganic bases such as sodium carbonate, potassium carbonate, calcium carbonate, sodium hydrogencarbonate, etc., tertiary amines such as triethylamine, tri(n-propyl)amine, tri(n-butyl)amine, diisopropylethylamine, cyclohexyl dimethylamine, pyridine, lutidine, γ-colidine, N,N-dimehtyl aniline, N-methyl piperidine, N-methyl pyrrolidine, N-methyl morpholine, etc., alkylene oxide such as propylene oxide, epichlorohydrin, etc. The compound (III) itself may be allowed to serve as a dehydrohalogenating agent as well. In this case, the compound (III) is used in an amount of not less than 2 mols relative to 1 mol of the compound (II) or a salt thereof. As the halogen shown by $R^4$ may be mentioned chlorine, bromine, iodine, etc., and preferably iodine. The compound (II) wherein $R^4$ is iodine can be produced easily by, for example, the method described in GB No. 2105719-A or a method analogous thereto.

The reaction product can be isolated and refined by conventional means such as solvent extraction, pH change, phasic transfer, salting out, crystallization, recrystallization, chromatography, etc. And, when a protective group or groups are contained in the reaction product, the protective group or groups may, if necessary, be removed to give the compound (I) or a salt thereof. As the means of removing the protective group, conventional ones, for example, means using an acid, a base or hydrazine, or reduction, or means using sodium N-methyldithiocarbamate, or the like can be suitably selected. More specifically, as the means of removing protective groups of an amino group, hydroxyl group and carboxyl group, means using an acid, means using a base or means resorting to reduction can be suitably selected depending on the kinds of the protective groups. In the case of resorting to the means using an acid, inorganic acids such as hydrochloric acid, sulfuric acid, phosphoric acid, etc., organic acids such as formic acid, trifluoroacetic acid, propionic acid, benzenesulfonic acid, P-toluenesulfonic acid, etc., and, besides, acid ion-exchange resins, etc. may suitably be employed as the acid depending on the kinds of the protective groups and other conditions. In the case of resorting to the means using a base, inorganic bases such as hydroxides or carbonates of an alkali metal e.g. sodium, potassium, etc. or an alkaline earth metal e.g. calcium, magnesium, etc., organic bases such as metal alkoxides, organic amines, quaternary ammonium salts, etc., and, besides, basic ion-exchange resins, etc. may suitably be employed as the base depending on the kinds of the protective groups and other conditions. In the case of resorting to the means of using the above-mentioned acids or bases, when a solvent is used, use may often be made of a hydrophilic organic solvent, water or a mixed solvent. In the case of resorting to reduction, such means as using a metal such as tin, zinc, etc. or a matallic compound such as chromium dichloride, chromium acetate, etc. and an organic or inorganic acid such as acetic acid, propionic acid, hydrochloric acid, etc., or a means of conducting reduction in the presence of a metal catalyst for catalytic reduction may be employed. As the catalyst usable for the catalytic reduction, use is made of, for example, a platinum catalyst such as platinum wire, platinum sponge, platinum black, platinum oxide, colloidal platinum, etc., a palladium catalyst such as palladium sponge, palladium black, palladium oxide, palladium barium sulfate, palladium barium carbonate, palladium carbon, palladium silica gel, colloidal palladium, etc., a nickel catalyst such as reducing nickel, nickel oxide, Urushibara nickel catalyst, etc. In the case of resorting to reduction using a metal and an acid, use is made of, for example, a metal compound of such metal as iron, chromium, etc. and an inorganic acid such as hydrochloric acid, etc. or an organic acid such as formic acid, acetic acid, propionic acid, etc. The reduction may usually be conducted in a solvent, and, for a catalytic reduction, for example, use is often made of, for example, alcohols such as methanol, ethanol, propyl alcohol, isopropyl alcohol, etc., ethyl acetate, etc. In the method of using a metal and an acid, use is often made of water, acetone, etc., and when the acid is in a liquid state, the acid itself can be used as solvent. The reaction temperatures in the means using an acid, a base or reduction, may usually be in the range of from those under cooling to those under warming. For removing the protective groups including silyl group, use may also be made of a compound containing fluorine ion such as tetrabutyl ammonium fluoride, potassium fluoride, etc. Further, when the amino-protective group is monochloroacetyl group, it can be readily removed by using, for example, thiourea or sodium N-methyl dithiocarbamate. In short, removal of the amino- or hydroxyl-protecting group can be carried out smoothly by per se conventional means.

And, when the compound to be obtained is a free acid or base, it may be converted by a conventional means to the corresponding pharmacologically acceptable salt, and, when the compound to be obtained is a salt, it may be converted by a conventional means to the corresponding free acid or base. These conversions can be carried out before or after the removal of the above-mentioned protective group or groups.

Method 2

A compound (I) or a salt thereof can also be produced by allowing a compound represented by the general formula:

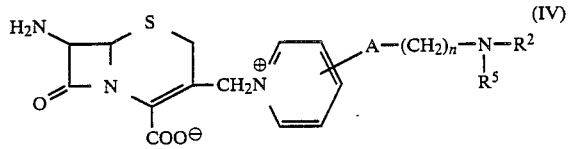

wherein symbols are of the same meanings as defined above, or a salt thereof to react with a compound represented by the general formula:

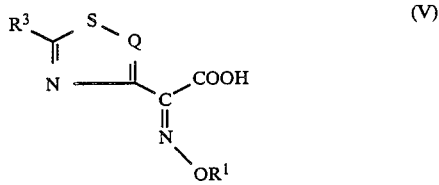

wherein symbols are of the same meanings as defined above, or a reactive derivative thereof at its carboxyl group, and upon necessity, in an optional order, removing the protective group or groups, converting the resultant salt to a corresponding free acid or free base, and/or converting the resultant free acid or free base to a corresponding pharmacologically acceptable salt. In the general formula (V), when an amino group is present in the substituent shown by $R^1$, this amino group is preferably protected. As the amino-protecting group, use may be made of those as defined for the above-mentioned $R^3$ and $R^5$. When a hydroxyl group is present, this hydroxyl group is preferably protected, and, as the hydroxyl-protecting group, use may be made of those as defined for the above-mentioned $R^1$. Further, when a carboxyl group is present, this carboxyl group is preferably protected and, as the carboxyl-protecting group, use may be made of those as defined for the above-mentioned $R^1$.

As the salts of the compound (IV), use is made of, for example, those with bases similar to those in the case of the salts of the afore-mentioned compound (II). These bases may be added together with the compound (IV), and the amount of the base ranges from about 1 to 10 mol equivalents, preferably from about 1 to 5 mol equivalents. The reactive derivatives at the carboxyl group of the compound (V) include, for example, acid halides, acid anhydrides, active amides, active esters, active thioesters, etc., which are more specifically stated as set forth below.

(1) Acid halides:
For example, acid chloride, acid bromide, etc. are used.

(2) Acid anhydrides:
For example, mono-lower($C_{1-4}$)alkyl carbonic acid mixed acid anhydrides, etc. are used.

(3) Active amides:
For example, amides formed with pyrazole, imidazole, 4-substituted (e.g. $C_{1-4}$alkyl) imidazole, dimethylpyrazole, benzotriazole, etc. are used.

(4) Active esters:
For example, esters such as methoxymethyl esters, benzotriazole esters, 4-nitrophenyl esters, 2,4-dinitrophenyl esters, trichlorophenyl esters, pentachlorophenyl esters, etc., as well as esters formed with 1-hydroxy-1H-2-pyridone, N-hydroxysuccinimide, N-hydroxyphthalimide or the like are used.

(5) Active thio esters:
For example, thio esters formed with, for example, heterocyclic thiols such as 2-pyridylthiol, 2-benzothiazolylthiol, bis-benzothiazol-2-yl disulfide, etc. are used.

In this reaction, the compound (V) or a reactive derivative at its carboxyl group may be used 1 mol or more relative to 1 mol of the compound (IV) or a salt thereof, preferably in a range of from about 1 mol to 4 mols. This reaction may be conducted usually in a solvent which is exemplified by water, ketones such as acetone, etc., ethers such as tetrahydrofuran, dioxane, etc., nitriles such as acetonitriles, etc., halogenated hydrocarbons such as dichloromethane, chloroform, 1,2-dichloroethane, etc., esters such as ethyl acetate, etc., amides such as dimethylformamide, dimethylacetamide, etc., among others. These solvents may be used singly or in combination of two or more of them in a suitable mixture ratio. When the compound (V) is used as the free acid, the reaction may preferably be carried out in the presence of a condensing agent which is exemplified by N,N'-dicyclohexylcarbodiimide, N-cyclohexyl-N'-morpholinoethylcarbodimiimide, N-cyclohexyl-N'-(4-diethylaminocyclohexyl)carbodiimide, N-ethyl-N'-(3-dimethylaminopropyl)carbodiimide, etc. The reaction can also be carried out in the presence of a base which includes, for example, alkali metal carbonates such as sodium carbonate, potassium carbonate, etc., tertiary amines such as triethylamine, tri-n-butylamine, N-methylmorpholine, N-methylpiperidine, N,N-dimethylaniline, pyridine, picoline, lutidine, etc. These bases serve to accelerate the reaction, to neutralize the acid formed during the reaction or to make the starting material to be readily soluble. The amount of such a base may usually be about 0.01 to 10 times mols relative to the compound (IV) or a salt thereof, preferably about 0.1 to 5 times mols. The reaction temperature is not specifically limitative, but it ranges usually from about $-30°$ C. to $50°$ C. The reaction time may range from several minutes to several ten hours (for example five minutes to 30 hours). The product obtained by this reaction can be isolated and refined by conventional means like in the case of Method 1. And, when a protecting group or groups are present in the product, the protecting group or groups can be removed, upon necessity, by conventional means as described in the foregoing to thereby give the compound (I) or a salt thereof.

Method 3

A compound (I) or a salt thereof can also be produced by allowing a compound represented by the general formula:

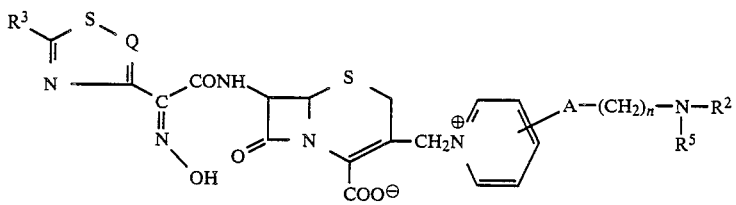

(VII)

wherein symbols are of the same meanings as defined above, or a salt thereof to react with a compound represented by the general formula: R¹'OH (VIII) R¹' stands for an optionally substituted lower alkyl group, or a reactive derivative thereof, and upon necessity, in an optional order, removing the protective group or groups, converting the resultant salt to a corresponding free acid or free base, and/or converting the resultant free acid or free base to a corresponding pharmacologically acceptable salt.

In the above general formula, as the optionally substituted lower alkyl group shown by R¹', use may be made of those as defined in R¹.

In the general formula (VIII), when an amino group exists in the substituent moiety shown by R¹', this amino group is preferably protected with a protecting group, and, as the amino-protecting group, use may be made of those as defined in $R^3$ and $R^5$; when a hydroxyl group exists, this hydroxyl group is preferably protected, and, as the hydroxyl-protecting group, use may be made of those as defined in the above R¹; and when a carboxyl group exists, this carboxyl group is preferably protected, and, as the carboxyl-protecting group, use may be made of those as defined in the above R¹.

This method is directed to the production of a compound (I) or a salt thereof by allowing a compound (VIII) represented by the general formula: R¹'OH or a reactive derivative thereof to react with a hydroxyimino compound (VII) or a salt thereof. The compound (VIII) can be used as it is or as a reactive derivative thereof. As the reactive derivative of the compound (VIII), use may be made of a derivative of R¹'OH having a group leaving together with the hydrogen atom of a hydroxyimino compound (VII), for example compounds represented by the general formula: R¹'Y, diazoalkane, dialkyl sulfate, etc. The symbol Y stands for halogen atom, mono-substituted sulfonyloxy group, etc. As the halogen of Y, use may be made of chlorine, bromine, iodine, etc. As the mono-substituted sulfonyloxy group of Y, use may be made of, among other, $C_{1-4}$alkylsulfonyloxy groups such as methanesulfonyloxy, ethanesulfonyloxy, etc. and $C_{6-10}$arylsulfonyloxy groups such as benzenesulfonyloxy, p-toluenesulfonyloxy, etc. Diazoalkane such as diazomethane, diazoethane, etc., dialkyl sulfate such as dimethyl sulfate, diethyl sulfate, etc. can also be used.

The compound (VII) or a salt thereof can be produced in accordance with the acylation described in Method 2 or the substitution reaction at the 3-position described in Method 1.

(1) When R¹'OH is used:

A compound (I) or a salt thereof is produced by allowing a hydroxyimino compound (VII) or a salt thereof to react with a compound (VIII) by using a suitable dehydrating agent which is exemplified by phosphorus oxychloride, thionyl chloride, dialkyl azodicarboxylate (usually employed in the coexistence of phosphine), N,N'-dicyclohexylcarbodiimide, etc., preferably diethyl azodicarboxylate in the coexistence of triphenylphosphine. The reaction using diethyl azodicarboxylate in the coexistence of triphenylphosphine is usually carried out in an anhydrous solvent which is, for example, the above-mentioned ethers, aromatic hydrocarbons, etc. Relative to 1 mol of a hydroxyimino compound (VII) or a salt thereof, about 1 to 1.5 mols each of a compound (VIII), ethyl azodicarboxylate and triphenylphosphine may be employed. The reaction temperature ranges from about 0° to 50° C., and the reaction time ranges from about 1 to 4 days.

(2) When R¹'Y is used:

The reaction between R'Y and a hydroxyimino compound (VII) or a salt thereof is usually etherification, which is carried out in a solvent. As the solvent, use may be made of ethers, esters, halogenated hydrocarbons, aromatic hydrocarbons, amides, ketones, nitriles, alcohols, water, etc. as exemplified in the section of Method 1, or a mixture of them, preferably a mixture of a water-miscible solvent and water (e.g. aqueous methanol, aqueous ethanol, aqueous acetone, aqueous dimethylsulfoxide, etc.). This reaction can also be allowed to proceed smoothly in the presence of a suitable base. As the base, use may be made of, among others, inorganic bases such as alkali metal salts e.g. sodium carbonate, sodium hydrogencarbonate, potassium carbonate, etc., and alkali metal hydroxides e.g. sodium hydroxide, potassium hydroxide. This reaction may be carried out in a buffer solution of pH 7.5 to 8.5. The molarities of the reagent R¹'Y and the base relative to 1 mol of the compound (VII) or a salt thereof are about 1 to 5 and about 1 to 10, respectively, preferably about 1 to 3 and about 1 to 5, respectively. The reaction temperature ranges from about −30° to 100° C., preferably about 0° to 80° C. The reaction time ranges from about 10 minutes to 15 hours, preferably about 30 minutes to 5 hours.

(3) When diazoalkane is used:

The reaction may usually be conducted in a solvent. As the solvent, use may be made of the above-mentioned ethers, aromatic hydrocarbons, etc. A hydroxyimino compound (VII) or a salt thereof is dissolved in a solvent, to which is added a solution of diazoalkane, whereupon the reaction proceeds. The reagent is used in an amount of about 1 mol to 10 mols relative to 1 mol of the compound (VII) or a salt thereof, preferably about 1 to 5 mols. The reaction is carried out at relatively low temperatures ranging from about −50° to 20° C., preferably about −30° to 0° C. The reaction time ranges from about 1 minute to 5 hours, preferably about 10 minutes to 1 hour.

(4) When dialkyl sulfate is used:

The reaction may usually be conducted in water or a mixture solvent of a water-miscible solvent and water. As the mixed solvent, those mentioned in the above Method 3 (2) may also be employed. This reaction may usually be conducted in the presence of an inorganic base which is, for example, an alkali metal hydroxide such as sodium hydroxyde, potassium hydroxide, etc.

The reagent is used in an amount of about 0.5 to 10 mols, preferably about 1 to 2 mols relative to 1 mol of the compound (VII) or a salt thereof. The reaction temperature ranges from about 20° C. to 100° C., preferably from about 50° C. to 100° C. The reaction time is in the range of from about 10 minutes to 5 hours, preferably from about 30 minutes to 3 hours.

After completion of the above-mentioned reaction, upon necessity, removal of the protecting group or groups, isolation or/and purification may be carried out to obtain the object compound (I) or a salt thereof.

Method 4

Furthermore, the compound (I) wherein Q is CH or a salt thereof can be produced by the following process. Namely, a compound represented by the general formula:

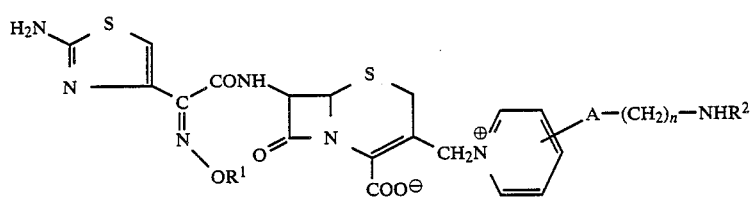

wherein symbols are of the same meanings as defined above, or a salt thereof can be produced by allowing a compound represented by the general formula:

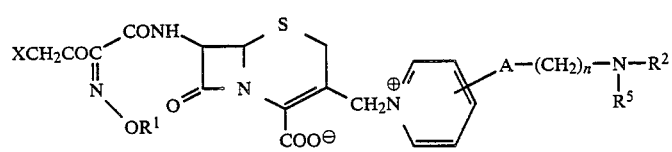

wherein X stands for halogen, and other symbols are of the same meanings as defined above, or a salt thereof to react with thiourea, and upon necessity, in an optional order, removing the protective group or groups, converting the resultant salt to a corresponding free acid or free base, and/or converting the resultant free acid or free base to a corresponding pharmacologically acceptable salt.

The group X in the compound (IX) stands for halogen such as chlorine, bromine, iodine, etc. As salts of the compound (IX), use may also be made of those of the compound (II) exemplified in the above Method 1 (inorganic base salts, ammonium salts, organic base salts, inorganic acid addition salts, organic acid addition salts, etc.). This reaction may be carried out usually in a solvent. As the solvent, use is made of, for example, ethers such as dioxane, tetrahydrofuran, diethylether, etc., alcohols such as methanol, ethanol, n-propanol, etc., amides such as dimethylformamide, dimethylacetamide, etc. Thiourea is used in an amount of usually about 1 to 5 mols, preferably about 1 to 3 mols relative to 1 mole of the compound (IX) or a salt thereof. The reaction is carried out in a temperature range of from about 0° C. to 100° C., preferably from about 20° C. to 60° C. The reaction time is usually about 30 minutes to 15 hours, preferably about 1 to 5 hours. The product obtained by this reaction can be isolated and refined by conventional means as in the case of Method 1. When a protecting group or groups exist in the product, the protecting group or groups are removed, upon necessity, by such a conventional means as mentioned above to thereby obtain the compound (I') or a salt thereof.

The starting compound (IX) or a salt thereof can be easily produced by allowing a compound represented by the general formula:

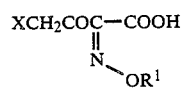

wherein symbols are of the same meanings as defined above, or a salt thereof or a reactive derivative thereof to react with the above-mentioned compound (IV) or a salt thereof in accordance with the method described in Method 2. The compound represented by the general formula:

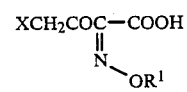     (IX)

or reactive derivatives thereof can be easily produced by a per se known means or those analogous thereto.

When the compound (I) isolated as above is a free acid or a free base, according to the conventional manner, it can be converted to a corresponding desired pharmacologically acceptable salt, and when the compound (I) is a salt, it can be converted to a corresponding free acid or free base, or, after converting to a desired salt, free acid or free base at the stage of a crude product, the crude product can be subjected to the above mentioned purification process to give the compound (I) or a salt thereof.

In the above Methods 1 to 4, the compound (I) (syn[Z]-isomer) may sometimes be obtained as a mixture with its anti[E]-isomer. For isolating the desired syn-isomer (i.e. the compound (I) or a salt thereof) from the mixture, a per se conventional means or an analogous one thereto may be employed, as exemplified by separation utilizing the difference in solubility, crystallizability, etc. or isolation by means of chromatography, etc.

The starting compound (II) or a salt thereof used in the above-mentioned Methods 1 and 2 can be obtained by the methods described in U.S. Pat. No. 4,520,194, No. 4,024,133, No. 4,033,950, No. 4,093,803 and No. 4,098,888. etc. or methods analogous thereto, for example. And, the compound (III) can be obtained by, for example, methods disclosed by the following Reference Examples 4 to 6 or methods analogous thereto or methods shown by the following scheme.

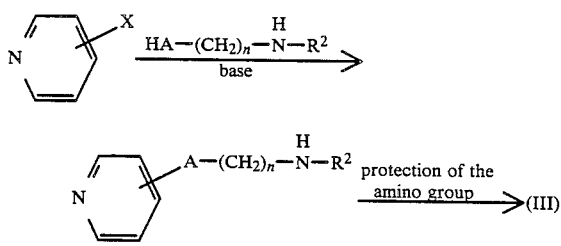

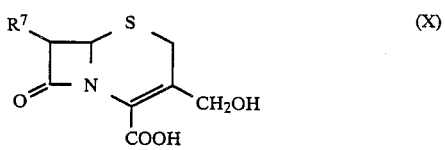

wherein symbols are of the same meanings as defined above.

The compound (IV) or a salt thereof can be produced by, for example, allowing a compound represented by the formula:

$$\underset{\text{COOH}}{\underset{\text{O}}{\overset{R^7}{\square}}\overset{S}{\underset{N}{\diagdown}}\overset{}{\diagup}\overset{}{\diagdown}CH_2OH} \quad (X)$$

wherein $R^7$ means a protected amino group as mentioned above, or a salt thereof to react with a compound (III), followed by removing the amino-protecting group. More concretely, the reaction between the compound (X) or a salt thereof and the compound (III) can be carried out in a similar manner to, for example, that between the compound (II) or a salt thereof and the compound (III) as mentioned above. After the reaction, the amino-protecting group or groups may be removed by such a method as described above, and then, upon necessity, the resultant may be converted to a salt by a conventional manner to give a compound (IV) or a salt thereof. As the salt of the compound (X), use is made of, for example, salts with bases employed for the salts of the compound (II). And, the compound (V) can be produced by the methods described in U.S. Pat. No. 4,024,133, No. 4,033,950, No. 4,520,194 and No. 4,098,888, etc. or methods analogous thereto.

The compounds (I) or salts thereof of this invention have a broad antibacterial spectrum, which can be used for the prophylaxis and therapy of various diseases caused by pathogenic bacteria in human beings and animals, for example, respiratory infections, urinary tract infections, etc. The characteristic features of the antibacterial spectrum of the compound (I) or a salt thereof are as follows.

(1) Remarkably high activities are shown against a variety of gram-negative bacteria.

(2) High activities are shown against gram-positive bacteria, e.g. *Staphylococcus aureus, Corynebacterium diphtheriae*, etc.

(3) Highly remarkable effects are observed against strains of *Pseudomonas aeruginosa* which are not sensitive to the therapy using conventional cephem-type antibiotics.

(4) Excellent activity is shown against meticillin-resistant *Staphylococcus aureus* as well.

(5) High activities are also observed against clinically isolated strains producing β-lactamases in a high degree belonging to, for example, *Citrobacter freundii, Enterobacter cloacae*. Especially against bacteria belonging to the genus Pseudomonas including *Pseudomonas aeruginosa*, though amino glycoside-type antibiotics such as amikacin, gentamycin, etc. have been used, the compounds (I) or salts thereof exhibit antibiotic activities comparable to these aminoglycosides, and their toxicities to human beings and animals are markedly lower than those of aminoglycosides, thus being of great advantage.

Besides, the compounds (I) or salts thereof of this invention are readily soluble in water and are excellent in stability, which have properties suitable for use especially as injections.

The Reference Examples, Working Examples and Test Examples are given below to illustrate the present invention in more detail, but these are merely examples and are not intended to limit the present invention in any way.

Elution in the column chromatography in the following Reference Examples and Working Examples was conducted under observation by means of TLC (thin layer chromatography). In the TLC observation, 60F$_{254}$ manufactured by Merck was used as the TLC plate, the solvent used as the eluent in the column chromatography was used as the developing solvent, and a UV detector was employed for detection. As the silica gel for the column, Kieselguhr 60 (230–400 mesh) also manufactured by Merck was used. "Cephadex" is a product of Pharmacia Fine Chemicals. XAD-II resin is a product of Rohm & Haas Co. NMR spectrum was measured by means of XL-100A(100 MHz), EM360(60 MHz), EM390(90 MHz) or T$_{60}$(60 MHz)-spectrometer, using tetramethylsilane as the internal or external standard, and all the δ values were shown by ppm. In mixed solvents, numerical values parenthesized mean the mixed ratios of each solvent by volume. Symbols in the Reference Examples and Working Examples have the following meanings.

s: singlet d: doublet t: triplet q: quartet ABq: AB type quartet dd: double doublet m: multiplet br.: broad J: coupling constant Reference Example 1

In 100 ml of water was suspended 10 g of 7-aminocephalosporanic acid (hereinafter abbreviated as "7-ACA"), to which was added gradually, while stirring under ice-cooling, a 2N aqueous solution of sodium hydroxide to keep the pH in a range from 12.5 to 13.4. The mixture was stirred for about 2 hours, which was then subjected to TLC. When disappearance of 7-ACA was confirmed, the pH was adjusted to 3.4 by the addition of 4N HCl. Precipitating crystals were collected by filtration, washed with water and acetone, followed by drying over phosphorus pentachloride under reduced pressure to give 5.4 g of 7β-amino-3-hydroxymethyl-3-cephem-4-carboxylic acid as pale yellow crystals.

IR (KBr)cm$^{-1}$: 3400, 3190, 3000, 2930, 2600, 1795, 1615.

Elementary Analysis $C_8H_{10}N_2O_4S\cdot\frac{1}{2}H_2O$: Calcd. (%): C, 41.33; H, 4.44; N, 12.05. Found (%): C, 41.29; H, 4.39; N, 11.84.

Reference Example 2

In 800 ml of a mixture (1:1) of water and tetrahydrofuran (hereinafter abbreviated as "THF") was suspended 16.9 g of 7β-amino-3-hydroxymethyl-3-cephem-4-carboxylic acid, to which was added, while stirring under ice-cooling, 27.72 g of sodium hydrogencarbonate. To the mixture was then added 29.4 of 2-(2-chloroacetamidothiazol-4-yl)-(Z)-2-methoxyiminoacetyl chloride hydrochloride gradually, followed by stirring for 30 minutes. To the reaction mixture were added 150 ml of water and 200 ml of ethyl acetate, which was shaken and then left standing to form two layers. The aqueous layer was taken, to which was added, while stirring under ice-cooling, 1N HCl to adjust the pH at 7.0. To the resultant was gradually added 18.9 g of sodium N-methyl dithiocarbamate while stirring at room temperature to remove the amino-protecting group (confirming by TLC). To the reaction mixture was added 300 ml of ethyl acetate, and the mixture was shaken and then left standing to form two layers. The aqueous layer was taken and concentrated to a volume of 70 ml under reduced pressure. The concentrate was subjected to a column chromatography using XAD-II (1 l), followed by elution with water. Fractions containing the object compound were collected and concentrated to a volume of 100 ml. To the concentrate was added, while stirring under ice-cooling, 4N HCl to adjust the pH at 2.5. Precipitating crystals were collected by filtration, washed with 100 ml of water, 50 ml of ethyl acetate and 50 ml of THF, followed by drying under reduced pressure to give 19.3 g of 7β-[2-(2-aminothiazol-4-yl)-(Z)-2-methoxyiminoacetamido]-3-hydroxymethyl-3-cephem-4-carboxylic acid.

IR (KBr)cm$^{-1}$: 3330, 3250, 2930, 1760, 1655.

NMR (d$_6$-DMSO)δ: 3.84(3H, s), 4.25(2H, s), 6.73(1H, s).

Elementary Analysis: C$_{14}$H$_{15}$N$_5$O$_6$S$_2$.½H$_2$O: Calcd. (%): C, 39.81; H, 3.82; N, 16.58. Found (%): C, 39.73; H, 3.74; N, 16.39.

In 150 ml of methanol was dissolved 1.85 g of tri-n-butylamine. To the solution was added 4.13 g of the compound as obtained above, while stirring at −20° C. The stirring was continued until the mixture became a clear solution, followed by distilling off methanol under reduced pressure. To the residue was added 200 ml of dry dichloromethane. The solvent was distilled off under reduced pressure, and the residue was dried to obtain 7β-[2-(2-aminothiazol-4-yl)-(Z)-2-methoxyiminoacetamido]-3-hydroxymethyl-3-cephem-4-carboxylic acid.tri-n-butylamine salt as a foamy product substantially quantitatively.

According to the manner as described above, the following compounds were obtained.

(a) 7β-[2-(2-Aminothiazol-4-yl)-(Z)-2-ethoxyiminoacetamido]-3-hydroxymethyl-3-cephem-4-carboxylic acid IR (KBr)cm$^{-1}$: 1765, 1665.

NMR (d$_6$-DMSO) δ: 1.23(3H, t, J=7 Hz), 4.11(2H, q, J=7 Hz), 4.26(2H, s), 6.72(1H, s).

(b) 7β-[2-(2-Aminothiazol-4-yl)-(Z)-2-ethoxyiminoacetamido]-3-hydroxymethyl-3-cephem-4-carboxylic acid.tri-n-butylamine salt (foamy powder).

Reference Example 3

To 100 ml of dichloromethane were added 1.01 g of 2-(5-amino-1,2,4-thiadiazol-3-yl)-(Z)-2-methoxyiminoacetic acid, 1.03 g of dicyclohexylcarbodiimide and 0.765 g of 1-hydroxybenzotriazole monohydrate. The mixture was stirred for 2 hours at room temperature, then precipitating crystals were collected by filtration. On the other hand, in 25 ml of dimethyl acetamide was suspended 1.26 g of sodium 7β-amino-3-hydroxymethyl-3-cephem-4-carboxylate. To the suspension were added the whole amount of the crystals as obtained above, and the mixture was stirred for 4 hours at room temperature and for 14 hours at 5° C. To the reaction mixture were added 30 ml of water and 100 ml of ethyl acetate, and the mixture was shaken. The aqueous layer was separated and concentrated under reduced pressure to a volume of about 10 ml, which was subjected to a silica gel (170 g) column chromatography. The column was washed with acetonitrile, followed by elution with a mixture of acetonitrile and water (4:1). The eluate was concentrated under reduced pressure to a volume of 20 ml. The concentrate was subjected to a column chromatography using XAD-II (200 ml), and the column was washed with water, followed by elution with 10% (V/V) ethanol. The eluate was concentrated under reduced pressure and the concentrate was lyophilized to give 1.2 g of sodium 7β-[2-(5-amino-1,2,4-thiadiazol-3-yl)-(Z)-2-methoxyiminoacetamido]-3-hydroxymethyl-3-cephem-4-carboxylate.

IR (KBr)cm$^{-1}$: 1760, 1665, 1600.

NMR (D$_2$O) δ: 4.18(3H, s), 4.37(2H, s)a, 5.30(1H, d, J=5 Hz), 5.92(1H, d).

Elementary Analysis: C$_{13}$H$_{13}$N$_6$NaO$_6$S$_2$.2H$_2$O. Calcd. (%): C, 33.05; H, 3.63; N, 17.79. Found (%): C, 33.09; H, 3.55; N, 17.61.

In the same manner as above, the following compound was obtained.

Sodium 7β-[2-(5-amino-1,2,4-thiadiazol-3-yl)-(Z)-2-ethoxyiminoacetamido]-3-hydroxymethyl-3-cephem-4-carboxylate.

IR (KBr)cm$^{-1}$: 3300, 1760, 1670, 1610.

NMR (d$_6$-DMSO) δ: 1.26(3H, t, J=7 Hz), 3.96(2H, ABq, J=12 Hz), 4.16(2H, q, J=7 Hz), 4.92(1H, d, J=5 Hz), 5.60(1H, dd, J=5.8 Hz).

Elementary Analysis: C$_{14}$H$_{15}$N$_6$NaO$_8$S$_2$.2H$_2$O: Calcd. (%): C, 34.57; H, 3.94; N, 17.28. Found (%): C, 34.76; H, 3.84; N, 17.18.

Reference Example 4

In 30 ml of ethanol was suspended 1.11 g of 4-mercaptopyridine, to which was added, while stirring under ice-cooling, 440 mg of sodium hydride (oily, 60 wt.%). The mixture was stirred at room temperature for 10 minutes, to which was then added 2.68 g of N-(3-bromopropyl)phthalimide, followed by stirring for 2 hours. The solvent was distilled off under reduced pressure. To the residue was added 100 ml of water. The mixture was subjected to extraction twice with 100 ml portions each of chloroform. The extracts were combined and dried over magnesium sulfate, followed by distilling off the solvent under reduced pressure. The residual solid matter was recrystallized from 40 ml of ethanol to give 1.40 g of colorless crystals. In 22 ml of ethanol was suspended 1.30 g of this crystals, to which was added 0.22 ml of hydrazine hydrate, followed by heating for 3 hours under reflux. The resultant was left standing for cooling, and precipitating crystals were filtered off. To the filtrate was added little by little 1.43 g of di-tert-butyl dicarbonate, and the mixture was stirred at room temperature for 30 minutes. The solvent was distilled off under reduced pressure. To the residue were added 100 ml of chloroform and 40 ml of water, and the mixture was shaken. The chloroform layer was taken and dried over magnesium sulfate. The solvent was distilled off under reduced pressure, and the residue was subjected to a silica gel (75 g) column chromatography. The column was developed with a mixture of hexane and ethyl acetate (1:1), followed by elution with ethyl acetate to give 915 mg of 4-(3-tert-butoxycarbonylaminopropylthio)pyridine as a pale yellow oily product.

IR (liquid film) cm$^{-1}$: 3350, 2980, 2950, 1685.

NMR(CDCl$_3$) δ: 1.44(9H, s), 1.70~2.10(2H, m), 2.99(2H, t, J=7 Hz), 3.13~3.40(2H, m), 4.7 4(1H, br. s), 7.03~7.17(2H, m), 8.33~8.47(2H, m).

This product solidified when being left standing under cooling, showing m.p. of 72° to 74° C.

Reference Example 5

In 150 ml of ethanol was suspended 5.56 g of 4-mercaptopyridine, to which was added 11.13 g of triethylamine to give a clear solution. To the solution was added 12.04 g of 3-bromopropylamine hydrobromide, and the mixture was stirred at room temperature for 1 hour. To the reaction mixture was added, while stirring, 16.37 g of di-tert-butyl dicarbonate little by little, followed by stirring for 30 minutes. The solvent was distilled off under reduced pressure. To the residue was added 200 ml of water, which was subjected to extraction with 200 ml of chloroform. The extract was dried over magnesium sulfate, from which the solvent was distilled off under reduced pressure. The residue was subjected to a silica gel (300 g) column chromatography. The column was developed with a mixture of hexane and ethyl acetate (1:1), followed by elution with ethyl acetate to give 6.26 g of 4-(3-tert-butoxycarbonylaminopropylthio)pyridine as pale yellow powder, m.p. 72° to 74° C.

IR(KBr)cm$^{-1}$: 3240, 3050, 2980, 1695.

Elementary Analysis: C$_{13}$H$_{20}$N$_2$O$_2$S: Calcd. (%): C, 58.18; H, 7.51; N, 10.44. Found (%): C, 58.58; H, 7.38; N, 10.24.

Reference Example 6

In 75 ml of ethanol was suspended 2.78 g of 4-mercaptopyridine, to which was added, while stirring under ice-cooling, 2.0 g of sodium hydride (oily, 60 wt.%). To the mixture was then added 5.12 g of 2-bromoethylamine hydrobromide, followed by stirring at room temperature for 20 hours. To the reaction mixture was added 8.19 g of di-tert-butyl dicarbonate, which was stirred for 30 minutes at room temperature, followed by distilling off the solvent under reduced pressure. To the residue was added 100 ml of chloroform, which was washed with water, followed by drying over magnesium sulfate. The solvent was distilled off under reduced pressure, and the residue was subjected to a silica gel (100 g) column chromatography. The column was developed with a mixture of ethyl acetate and hexane (1:1), followed by elution with ethyl acetate. The eluate was concentrated under reduced pressure to give 4.74 g of 4-(2-tert-butoxycarbonylaminoethylthio)pyridine as a yellow oily product.

IR(liquid film)cm$^{-1}$: 3330, 2980, 1695.

NMR(CDCl$_3$)δ: 1.46 (9H, s), 3.00~3.53 (4H, m), 5.10 (1H, br. s), 7.12~7.25 (2H, m), 8.35~8.48 (2H, m).

Reference Example 7

In 100 ml of ethanol were suspended 6.66 g of 4-mercaptopyridine and 16.9 g of N-(4-bromobutyl)phthalimide. To the suspension was added 9.09 g of triethylamine, and the mixture was stirred at room temperature for 4 hours. The solvent was distilled off under reduced pressure. To the residue was added 300 ml of water, and the mixture was subjected to extraction twice with dichloromethane. The extract solutions were combined, washed with an aqueous saline solution, then dried over magnesium sulfate. The solvent was distilled off under reduced pressure, and the residue was subjected to a silica gel (500 g) column chromatography, using as the developer a mixture of hexane and ethyl acetate (1:2), followed by elution with ethyl acetate. The eluate was concentrated under reduced pressure. To the concentrate were added ethyl acetate and hexane. Resulting powders were collected by filtration to give N-[4-(4-pyridylthio)butyl]phthalimide as a colorless powdery product, m.p. 106.5°-107.5° C.

IR(KBr)cm$^{-1}$: 1770, 1710, 1575.

NMR(CDCl$_3$)δ: 1.5 to 2.1 (4H, m), 3.01 (2H, t, J=6.5 Hz), 3.72 (2H, t, J=6.5 Hz), 7.0 to 7.1 (2H, m), 7.6 to 7.9 (4H, m), 8.3 to 8.4 (2H, m).

Elementary Analysis for C$_{17}$H$_{16}$N$_2$O$_2$S: Calcd. (%): C, 65.36; H, 5.16; N, 8.97. Found (%): C, 65.29; H, 5.12; N. 8.94.

Reference Example 8

In 150 ml of ethanol was suspended 4.69 g of N-[4-(4-pyridylthio)butyl]phthalimide. To the suspension was added 0.765 ml of hydrazine hydrate, and the mixture was heated for 2 hours under reflux. After standing for cooling, precipitating crystals were filtered off, and the filtrate was concentrated under reduced pressure. To the concentrate were added 150 ml of dichloromethane and 4.92 g of di-tert-butyl dicarbonate.

The mixture was stirred at room temperature for 1.5 hours. The reaction mixture was washed with water, dried over magnesium sulfate and then concentrated under reduced pressure. The concentrate was subjected to a silica gel (150 g) column chromatography, using a mixture of hexane and ethyl acetate (1:1) as the developer, followed by elution with ethyl acetate. The eluate was concentrated under reduced pressure to give 4.0 g of 4-(4-tert-butoxycarbonylaminobutylthio)pyridine as a yellow oily product.

IR(liquid film)cm$^{-1}$: 3350, 2980, 2940, 1695, 1575.

NMR(CDCl$_3$)δ: 1.44 (9H, s), 1.5 to 1.9 (4H, m), 2.9 to 3.3 (4H, m), 4.67 (1H, br.s), 7.0 to 7.2 (2H, m), 8.3 to 8.5 (2H, m).

Reference Example 9

In the same manner as Reference Example 2, 7β-[2-(2-aminothiazol-4-yl)-(Z)-2-allyloxyiminoacetamido]-3-hydroxymethyl-3-cephem-4-carboxylic acid was obtained as a colorless powdery product.

IR(KBr)cm$^{-1}$: 3530, 3260, 1770, 1660, 1550.

NMR(d$_6$-DMSO)δ: 3.53 (2H, s), 4.24 (2H, s), 4.58 (2H, d, J=5 Hz), 5.05 to 5.4 (3H, m), 5.65 to 6.2 (2H, m), 6.70 (1H, s), 7.16 (2H, s), 9.57 (1H, d, J=9 Hz).

In the same manner as Reference Example 2, this product can be converted to a corresponding tri-n-butyl amine salt.

Reference Example 10

In 180 ml of water was suspended 5.756 g of 7β-amino-3-hydroxymethyl-3-cephem-4-carboxylic acid. To the suspension was added a 1N aqueous solution of sodium hydroxide under ice-cooling to adjust the pH to 7.6, whereupon the suspension dissolved completely. To this solution were added 11.965 g of 2-(2-aminothiazol-4-yl)-(Z)-2-(1-tert-butoxycarbonyl-1-methylethoxyamino)acetic acid benzothiazol-2-yl thioester and 220 ml of tetrahydrofuran. The mixture was stirred at room temperature for 24 hours. Tetrahydrofuran was distilled off under reduced pressure, and the remaining aqueous solution was washed with 200 ml of ethyl acetate. The aqueous layer was concentrated under reduced pressure to a volume of 100 ml, and the concentrate was subjected to an HP-20 (250 ml) column chromatography. The column was washed with 1 l of water, followed by elution with 2.5 l of 10%(V/V) ethanol. The eluate was concentrated to a volume of 200 ml. The concentrate was subjected to filtration. The filtrate was lyophilized to give 9.3 g of 7β-[2-(2-aminothiazol-4-yl)-(Z)-2-(1-tert-butoxycarbonyl-1-methylethoxyimino)acetamido]-3-hydroxymethyl-3-cephem-4-carboxylic acid.sodium salt as a pale yellow powder product.

IR(KBr)cm$^{-1}$: 3300, 2975, 2925, 1750, 1670, 1600.

NMR(D$_2$O)δ: 1.58 (9H, s), 1.67 (6H, s), 3.66 (2H, ABq, J=18 Hz), 4.37 (2H, s), 5.32 (1H, d, J=5 Hz), 5.93 (1H, d, J=5 Hz), 7.15 (1H, s).

Elementary Analysis for C$_{21}$H$_{26}$N$_5$O$_8$NaS$_2$.2.5H$_2$O: Calcd. (%): C, 41.44; H, 5.13; N, 11.51. Found (%): C, 41.39; H, 4.99; N, 11.65.

EXAMPLE 1

7β-[2-(2-aminothiazol-4-yl)-(Z)-2-methoxyiminoacetamido]-3-{[4-(3-aminopropylthio)-1-pyridinium]methyl}-3-cephem-4-carboxylate hydrochloride

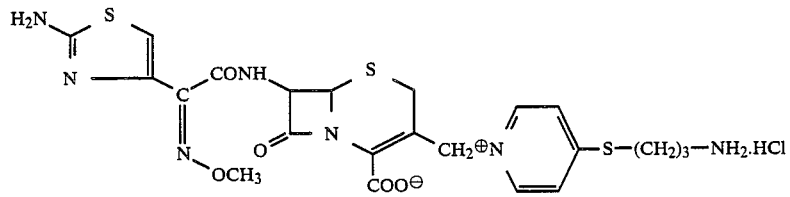

In 10 ml of dimethylformamide were dissolved 599 mg of 7β-[2-(2-aminothiazol-4-yl)-(Z)-2-methoxyiminoacetamido]-3-hydroxymethyl-3-cephem-4-carboxylic acid.tri-n-butylamine salt and 805 mg of 4-(3-tert-butoxycarbonylaminopropylthio)pyridine. The solution was cooled to −20° C., to which was added 600 mg of o-phenylene phosphate. The mixture was stirred for 1 hour while raising the temperature gradually to 0° C. The reaction mixture was subjected to a silica gel (80 g) column chromatography. The column was washed with acetonitrile and a mixture of acetonitrile and water (8:1) in sequence, followed by elution with a mixture of acetonitrile and water (6:1). The eluate was concentrated under reduced pressure, followed by lyophilization to give 270 mg of yellow powder. This product was added to 10 ml of 3N HCl, which was stirred for 1 hour at room temperature, followed by addition of a 1N aqueous solution of sodium hydroxide under ice-cooling to adjust the pH to 3.8. The resultant was subjected to an XAD-II (100 ml) column chromatography, followed by elution with water. The eluate was concentrated under reduced pressure, and the concentrate was lyophilized to give 76 mg of the subject compound as a colorless powdery product.

IR(KBr)cm$^{-1}$: 1770, 1660, 1620.

NMR(D$_2$O)δ: 2.05~2.75 (2H, m), 3.13~3.90 (6H, m), 4.05 (3H, s), 5.33 (2H, ABq, J=15 Hz), 5.34 (1H, d, J=4.5 Hz), 5.87 (1H, dd, J=4.5 Hz), 7.02 (1H, s), 7.85 (2H, d, J=6.5 Hz), 8.63 (2H, d, J=6.5 Hz).

Elementary Analysis: C$_{22}$H$_{25}$N$_7$O$_5$S$_3$.HCl.5H$_2$O: Calcd. (%): C, 38.28; H, 5.26; N, 14.21. Found (%): C, 38.52; H, 5.01; N, 14.32.

EXAMPLE 2

7β-[2-(2-aminothiazol-4-yl)-(Z)-2-ethoxyiminoacetamido]-3-{[4-(3-aminopropylthio)-1-pyridinium]methyl}-3-cephem-4-carboxylate hydrochloride

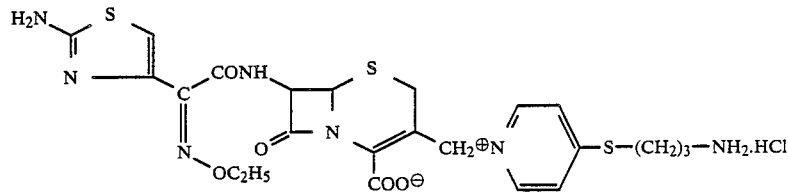

In 10 ml of dimethylformamide were dissolved 613 mg of 7β-[2-(2-aminothiazol-4-yl)-(Z)-2-ethoxyiminoacetamido]-3-hydroxymethyl-3-cephem-4-carboxylic acid.tri-n-butylamine salt and 805 mg of 4-(3-tert-butoxycarbonylaminopropylthio)pyridine. The solution was cooled to −20° C., to which was added 600 mg of o-phenylene phosphate. The mixture was stirred for 1 hour while raising the temperature gradually to 0° C. The reaction mixture was subjected to a silica gel (80 g) column chromatography. The column was washed with acetonitrile and a mixture of acetonitrile and water (8:1) in sequence, followed by elution with a mixture of acetonitrile and water (6:1). The eluate was concentrated under reduced pressure, followed by lyophilization to give 370 mg of yellow powder. This product was added to 10 ml of 3N HCl, and the mixture was stirred at room temperature for 1 hour, followed by addition of a 3N aqueous solution of sodium hydroxide under ice-cooling to adjust the pH to 3.5. The resultant was subjected to an XAD-II (100 ml) column chromatography, followed by elution with water. The eluate was concentrated under reduced pressure and then lyophilized to give 136 mg of the subject compound as colorless powder.

IR(KBr)cm$^{-1}$: 1780, 1665, 1620.

NMR(D$_2$O)δ: 1.38 (3H, t, J=7 Hz), 2.06~2.45 (2H, m), 3.17~3.90 (6H, m), 4.39 (2H, q, J=7 Hz), 5.38 (1H, d, J=4.5 Hz), 5.38 (2H, ABq, J=15 Hz), 5.93 (1H, d, J=4.5 Hz), 7.13 (1H, s), 7.91 (2H, d, J=7 Hz), 8.68 (2H, d, J=7 Hz).

EXAMPLE 3

7β-[2-(5-amino-1,2,4-thiadiazol-3-yl)-(Z)-2-methoxyiminoacetamido]-3-{[4-(3-aminopropylthio)-1-pyridinium]methyl}-3-cephem-4-carboxylate hydrochloride

EXAMPLE 4

7β-[2-(2-aminothiazol-4-yl)-(Z)-2-methoxyiminoacetamido]-3-{[4-(2-aminoethylthio)-1-pyridinium]methyl}-3-cephem-4-carboxylate hydrochloride

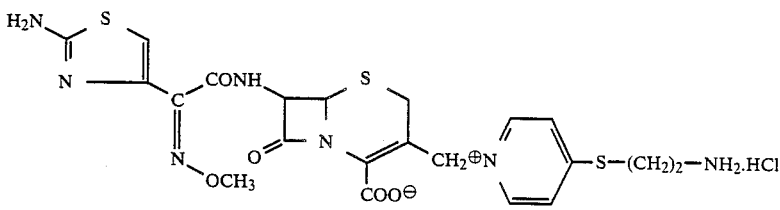

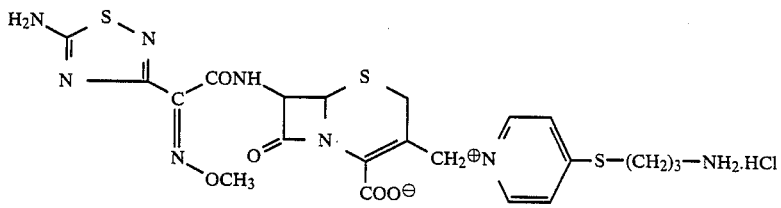

In 10 ml of dimethylformamide were dissolved 436 mg of sodium 7β-[2-(5-amino-1,2,4-thiadiazol-3-yl)-(Z)-2-methoxyiminoacetamido]-3-hydroxymethyl-3-cephem-4-carboxylate and 805 mg of 4-(3-tert-butoxycarbonylaminopropylthio)pyridine. The solution was cooled to −20° C., to which was added 600 mg of o-phenylene phosphate. The mixture was stirred for 1 hour while gradually raising the temperature to 0° C. The reaction mixture was subjected to a silica gel (80 g) column chromatography, and the column was developed with acetonitrile and mixtures of acetonitrile and water (8:1 and 7:1) in sequence, followed by elution of a mixture of acetonitrile and water (6:1). The eluate was concentrated under reduced pressure and then lyophilized to give 300 mg of a pale yellow powdery product. This product was added to 10 ml of 3N HCl, and the mixture was stirred at room temperature for 1 hour, followed by addition of a 3N aqueous solution of sodium hydroxide under ice-cooling to adjust the pH to 3.8. The resultant was subjected to an XAD-II (100 ml) column chromatography, followed by elution with water. The eluate was concentrated under reduced pressure, and the concentrate was lyophilized to give 112 mg of the subject compound as colorless powder.

IR(KBr)cm$^{-1}$: 1175, 16605 1625.

NMR(D$_2$O)δ: 2.05~2.43 (2H, m), 3.13~3.88 (6H, m), 4.14 (3H, s), 5.35 (1H, d, J=5 Hz), 5.38 (2H, ABq, J=14 Hz), 5.94 (1H, d, J=5 Hz), 7.89 (2H, d, J=6.5 Hz), 8.67 (2H, d, J=6.5 Hz).

Elementary Analysis: C$_{21}$H$_{24}$N$_8$O$_5$S$_3$.HCl.4½H$_2$O: Calcd. (%): C, 36.97; H, 5.02; N, 16.43. Found (%): C, 37.18; H, 4.67; N, 16.61.

In 15 ml of dimethylformamide were dissolved 898 mg of 7β-[2-(2-aminothiazol-4-yl)-(Z)-2-methoxyiminoacetamido]-3-hydroxymethyl-3-cephem-4-carboxylic acid tri-n-butylamine salt and 1.145 g of 4-(2-tert-butoxycarbonylaminoethylthio)pyridine, and the solution was cooled to −20° C., to which was added 901 mg of ethyl o-phenylene phosphate. The mixture was stirred for 1 hour while raising the temperature gradually up to 0° C. The reaction mixture was subjected to a silica gel (100 g) column chromatography, and the column was washed with acetonitrile and a mixture of acetonitrile and water (8:1) in sequence, followed by elution with a mixture of acetonitrile and water (5:1). The eluate was concentrated under reduced pressure, followed by lyophilization to give 370 mg of a yellow powdery product. This product was added to 10 ml of 3N HCl, and the mixture was stirred for 1 hour at room temperature. To the resultant was added under ice-cooling a 1N aqueous solution of sodium hydroxide to adjust the pH to 3.8. The resultant was subjected to an XAD-II (150 ml) column chromatography, followed by elution with water. The eluate was concentrated under reduced pressure, followed by lyophilization to give 110 mg of the subject compound as a colorless powdery product.

IR(KBr)cm$^{-1}$: 1775, 1655, 1625.

NMR(D$_2$O)δ: 3.16~3.92 (6H, m), 4.08 (3H, s), 5.37 (1H, d, J=4.5 Hz), 5.39 (2H, ABq, J=15 Hz). 5.90 (1H, d, J=4.5 Hz), 7.05 (1H, s), 7.94 (2H, d, J=6.5 Hz), 8.74 (2H, d, J=6.5 Hz).

Elementary Analysis: C$_{21}$H$_{23}$N$_7$O$_5$S$_3$.HCl.4½H$_2$O: Calcd. (%): C, 37.81; H, 4.99; N, 14.70. Found (%): C, 37.75; H, 4.87; N, 14.67.

EXAMPLE 5

7β-[2-(2-Aminothiazol-4-yl)-(Z)-2-ethoxyiminoacetamido]-3-{[4-(2-aminoethylthio)-1-pyridinium]methyl}-3-cephem-4-carboxylate hydrochloride

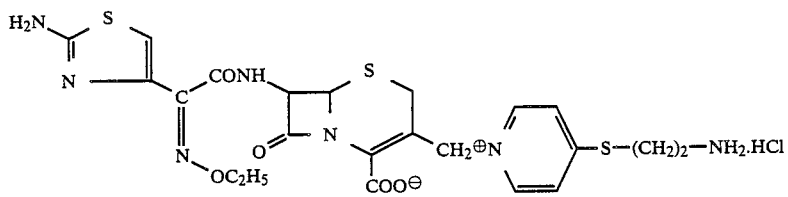

In the same manner as Example 4, the above-titled compound was obtained as a colorless powdery product.

IR(KBr)cm$^{-1}$: 1775, 1665, 1630.

NMR(D$_2$O)δ: 1.38 (3H, t, J=7 Hz), 3.25 to 4.0 (6H, m), 4.43 (2H, q, J=7 Hz), 5.40 (1H, d, J=5 Hz), 5.46 (2H, ABq, J=15 Hz), 5.95 (1H, d, J=5 Hz), 7.21 (1H, s), 7.97 (2H, d, J=6.5 Hz), 8.72 (2H, d, J=6.5 Hz).

EXAMPLE 6

7β-[2-(2-Aminothiazol-4-yl)-(Z)-2-methoxyiminoacetamido]-3-{[4-aminobutylthio)-1-pyridinium]methyl}-3-cephem-4-carboxylate hydrochloride

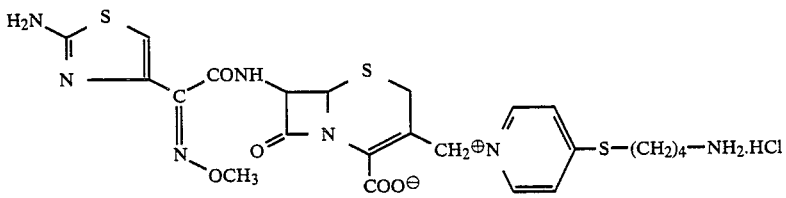

In the same manner as Example 1, the above-titled compound was obtained as a colorless powdery product.

IR(KBr)cm$^{-1}$: 1770, 1660, 1625, 1530.

NMR(D$_2$O)δ: 1.75 to 2.15 (4H, m), 3.0 to 3.95 (6H, m), 4.07 (3H, s), 5.33 (2H, ABq, J=15 Hz), 5.36 (1H, d, J=5 Hz), 7.04 (1H, s), 7.86 (2H, d, J=7 Hz), 8.64 (2H, d, J=7 Hz).

EXAMPLE 7

7β-[2-(2-Aminothiazol-4-yl)-(Z)-2-ethoxyiminoacetamido]-3-{[4-(4-aminobutylthio)-1-pyridinium]methyl}-3-cephem-4-carboxylate hydrochloride

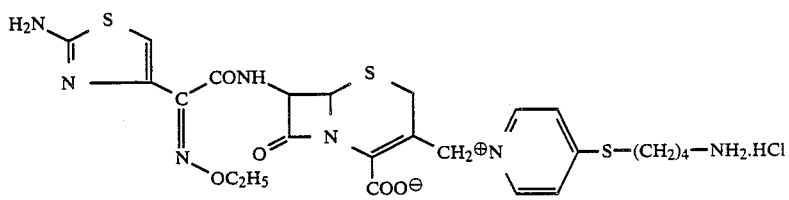

In the same manner as Example 2, the above-titled compound was obtained as a pale yellow powdery product.

IR(KBr)cm$^{-1}$: 1770, 1660, 130, 1530.

NMR(D$_2$O)δ: 1.37 (3H, t, J=7 Hz), 1.8 to 2.15 (4H, m), 3.0 to 3.9 (6H, m), 4.36 (2H, q, J=7 Hz), 5.35 (2H, ABq, J=15 Hz), 5.36 (1H, d, J=5 Hz), 5.91 (1H, d, J=5 Hz), 7.07 (1H, s), 7.86 (2H, d, J=7 Hz), 8.62 (2H, d, J=7 Hz).

EXAMPLE 8

7β-[2-(5-Amino-1,2,4-thiadiazol-3-yl)-(Z)-2-ethoxyiminoacetamido]-3-{[4-(3-aminopropylthio)-1-pyridinium]methyl}-3-cephem-4-carboxylate hydrochloride

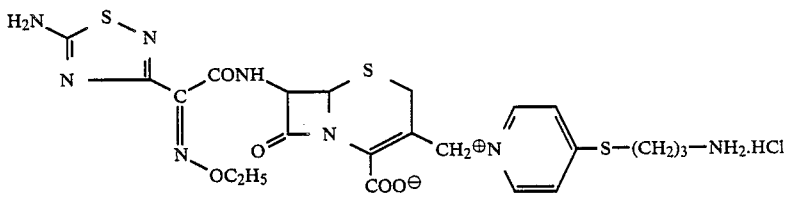

In the same manner as Example 3, the above-titled compound was obtained as a colorless powdery product.

IR(KBr)cm$^{-1}$: 1775, 1670, 1630.

NMR(D$_2$O)δ: 1.38 (3H, t, J=7 Hz), 2.05 to 2.45 (2H, m), 3.1 to 3.9 (6H, m), 4.41 (2H, q, J=7 Hz), 5.37 (1H, d, J=5 Hz), 5.38 (2H, ABq, J=15 Hz), 5.95 (1H, d, J=5 Hz), 7.88 (2H, d, J=6.5 Hz), 8.66 (2H, d, J=6.5 Hz).

EXAMPLE 9

7β-[2-(5-Amino-1,2,4-thiadiazol-3-yl)-(Z)-2-methoxyiminoacetamido]-3-{[4-(4-aminobutylthio)-1-pyridinium]methyl}-3-cephem-4-carboxylate hydrochloride

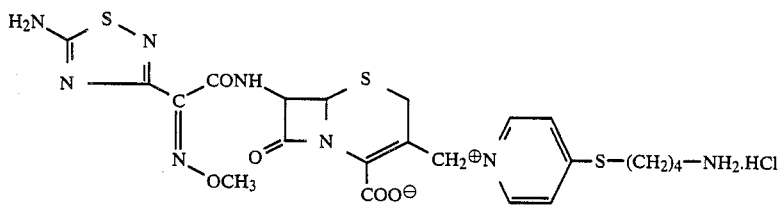

In the same manner as Example 3, the above-titled compound was obtained as a colorless powdery product.

IR(KBr)cm$^{-1}$: 1770, 1660, 1620.

NMR(D$_2$O)δ: 1.75 to 2.15 (4H, m), 3.0 to 3.9 (6H, m), 4.15 (3H, s), 5.36 (1H, d, J=5 Hz), 5.37 (2H, ABq, J=15 Hz), 5.94 (1H, d, J=5 Hz), 7.85 (2H, d, J=6.5 Hz), 8.63 (2H, d, J=6.5 Hz).

EXAMPLE 10

7β-[2-(2-Aminothiazol-4-yl)-(Z)-2-allyloxyiminoacetamido]-3-{[4-(3-aminopropylthio)-1-pyridinium]methyl}-3-cephem-4-carboxylate hydrochloride

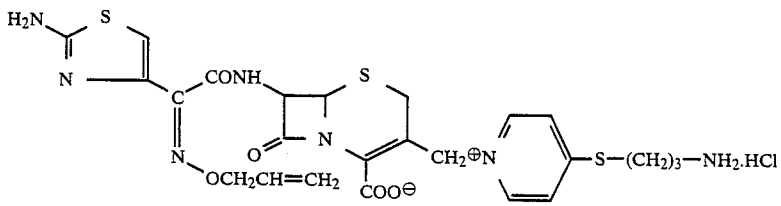

In 8 ml of dimethyformamide were dissolved 936 mg of 7β-[2-(2-aminothiazol-4-yl)-(Z)-2-allyloxyiminoacetamido]-3-hydroxymethyl-3-cephem-4-carboxylic acid tri-n-butylamine salt and 1.21 g of 4-(3-tert-butoxycarbonylaminopropylthio)pyridine. The solution was cooled to −20° C., to which was added 900 mg of ethyl o-phenylenephosphate. The mixture was stirred for 1 hour, while raising the temperature gradually to 0° C. The reaction mixture was subjected to a silica gel (100 g) column chromatography. The column was washed with 1 l of acetonitrile and a mixture of acetonitrile and water (19:1, 1 l; 9:1, 500 ml) in sequence, followed by elution with 500 ml of a mixture of acetonitrile and water (17:3). The eluate was concentrated under reduced pressure to a volume of 70 ml, and the concentrate was subjected to filtration. The filtrate was concentrated under reduced pressure, followed by lyophilization to give 450 mg of a pale yellow powdery substance. This substance was added to 12 ml of 3N HCl, and the mixture was stirred for 1 hour at room temperature. The resultant was subjected to filtration, and the filtrate was adjusted to pH 3.7 with a 3N aqueous solution of sodium hydroxide under ice-cooling. The resultant solution was subjected to an XAD-II (80 ml) column chromatography. The column was washed with water and then elution was carried out with 400 ml of 5% (V/V) ethanol. The eluate was concentrated under reduced pressure to a volume of 50 ml. The concentrate was subjected to filtration, and the filtrate was lyophilized to obtain 214 mg of the above-titled compound as a colorless powdery product.

IR(KBr)cm$^{-1}$: 3350, 3100, 3000, 1770, 1620.

NMR(D$_2$O+DCl)δ: 2.1 to 2.45 (2H, m), 3.2 to 3.95 (6H, m), 5.2 to 5.9 (5H, m), 5.98 (1H, d, J=5 Hz), 6.0 to 6.4 (1H, m), 7.26 (1H, s), 7.95 (2H, d, J=7 Hz), 8.69 (2H, d, J=7 Hz).

EXAMPLE 11

7β-[2-(2-Aminothiazol-4-1)-(Z)-2-(1-carboxy-1-methylethoxyimino)acetamido]-3-{[4-(3-aminopropylthio)-1-pyridinium]methyl}-3-cephem-4-carboxylate

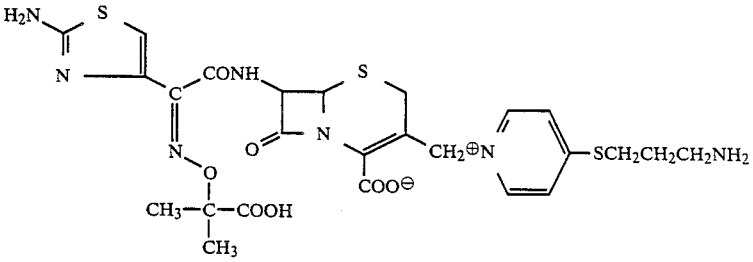

In 50 ml of dimethylformamide were dissolved 9.1 g of 7β-[2-(2-aminothiazol-4-yl)-(Z)-2-(1-tert-butoxycarbonyl-1-methylethoxyimino)acetamido]-3-hydroxymethyl-3-cephem-4-carboxylic acid.sodium salt and 13 g of 4-(3-tert-butoxycarbonylaminopropylthio)pyridine. To the solution was added 15 g of sodium sulfate, and the mixture was cooled to −20° C. To the resultant was added dropwise, while stirring at the same temperature, 9.69 g of ethyl o-phenylene phosphate. The mixture was stirred for 1.5 hours while its temperature was gradually raised to 0° C. The reaction mixture was then subjected to a silica gel (280 g) column chromatography. The column was washed with 1.5 l of acetonitrile and 1.5 l of a mixture of acetonitrile and water (19:1). Elution was then carried out with a mixture of acetonitrile and water (9:1, 2 l; 17.3, 1 l). The eluate was concentrated under reduced pressure, followed by lyophilization to give 8.42 g of a pale yellow powdery substance. This substance was dissolved in 40 ml of dimethylformamide, and the solution was subjected to a silica gel (250 g) column chromatography. The column was washed with acetonitrile and a mixture of acetonitrile and water (9:1). Elution was then carried out with 1.5 l of a mixture of acetonitrile and water (17:3). The eluate was concentrated under reduced pressure, followed by lyophilization to give 5.1 g of a pale yellow powdery substance. This substance was added to 50 ml of 6N HCl, and the mixture was stirred at room temperature for 1.5 hours. The mixture was adjusted to pH 3.5 with a 3N aqueous solution of sodium hydroxide under cooling with ice-water, after which the resultant was subjected to an XAD-2 (250 ml) column chromatography. The column was washed with 600 ml of water and then elution was carried out with 1 l of 10% (V/V) ethanol. The eluate was concentrated under reduced pressure, and the concentrate was subjected to filtration. The filtrate was lyophilized to give 2.5 g of the above-titled compound as a pale yellow powdery product.

IR(KBr)cm$^{-1}$: 3300, 1770, 1620, 1530.

NMR(D$_2$O+DCl)δ: 1.69 (6H, s), 2.1 to 2.45 (2H, m), 3.2 to 3.95 (6H, m), 5.47 (1H, d, J=5 Hz), 5.53 (2H, ABq, J=15 Hz), 6.01 (1H, d, J=5 Hz), 7.32 (1H, s), 7.95 (2H, d, J=7 Hz), 8.70 (2H, d, J=7 Hz).

Test Example 1

MIC (minimum inhibitory concentration) value of the compound as obtained in Example 2 is shown below.

(a) Method of Determination

The MIC value of the test compound was determined by agar dilution method. More specifically, 1.0 ml of an aqueous solution of the test compound diluted serially was poured into a petri dish, to which were added 9.0 ml of trypticase soy agar, followed by mixing. On the mixed agar plate was spread a suspension of the test microorganism (ca. 10$^8$ CFU/ml), which was incubated at 37° C. for 18 hours. The lowest concentration of the test compound completely inhibiting the growth of the test microorganism was expressed by MIC (minimum inhibitory concentration).

(b) Test Microorganisms (1) *Staphylococcus aureus* 1840
(2) *Escherichia coli* T7

MIC values of the test compound are shown in Table 1.

TABLE 1

| Test Organisms | MIC value (μg/ml) Test Compound Compound Described in Example 2 |
|---|---|
| (1) | 0.78 |
| (2) | 0.2 |

What we claim is:

1. A compound of the formula:

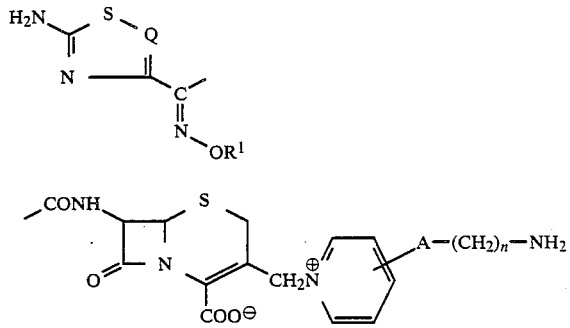

wherein Q stands for a nitrogen atom or CH, R$^1$ stands for a hydrogen atom or an optionally substituted lower alkyl group, A stands for a sulfur atom or NH, and n denotes an integral number ranging from 2 to 4, or a pharmaceutically acceptable salt thereof.

2. A compound as claimed in claim 1, wherein Q is CH.

3. A compound as claimed in claim 1, wherein Q is a nitrogen atom.

4. A compound as claimed in claims 1 to 3, wherein A is a sulfur atom.

5. A compound as claimed in claim 1 of the formula:

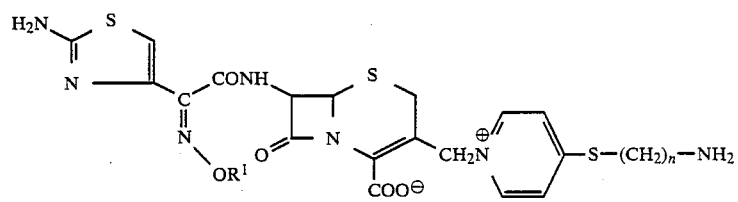

wherein R$^1$ and n are as defined in claim 1, or a salt thereof.

6. A compound as claimed in claim 1, wherein R$^1$ is a straight-chain or branched alkyl group having 1 to 6 carbon atoms which may be substituted by one to three substituents selected from a vinyl group, carboxyl group, C$_{1-6}$-alkoxycarbonyl group, amino group, hydroxyl group and halogen.

7. A compound as claimed in claim 1, which is 7β-[2-(2-aminothiazol-4-yl)-(Z)-2-ethoxyiminoacetamido]-3-{[4-(3-aminopropylthio)-1-pyridinium]methyl}-3-cephem-4-carboxylate.

8. An antimicrobial composition which contains an effective antimicrobial amount of a compound of the formula

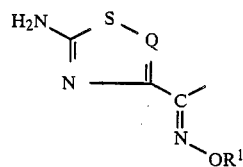
-continued
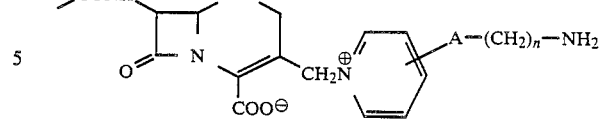
wherein Q stands for a nitrogen atom or CH, $R^1$ stands for a hydrogen atom or an optionally substituted lower alkyl group, A stands for a sulfur atom or NH, and n denotes an integral number ranging from 2 to 4, or a pharmaceutically acceptable salt thereof, together with a suitable carrier or carriers.
* * * * *